US00PP28282P3

(12) United States Plant Patent
Tan

(10) Patent No.: US PP28,282 P3
(45) Date of Patent: Aug. 15, 2017

(54) ***HIBISCUS* PLANT NAMED 'TAHI16'**

(50) Latin Name: *Hibiscus×moscheutos*
Varietal Denomination: TAHI16

(71) Applicant: Alain Tan, Montauban (FR)

(72) Inventor: Alain Tan, Montauban (FR)

( * ) Notice: Subject to any disclaimer, the term of this patent is extended or adjusted under 35 U.S.C. 154(b) by 21 days.

(21) Appl. No.: 14/757,377

(22) Filed: Dec. 22, 2015

(65) Prior Publication Data

US 2017/0094861 P1 Mar. 30, 2017

(30) Foreign Application Priority Data

Sep. 29, 2015 (EM) ..... 2015/2259

(51) Int. Cl.
*A01H 5/02* (2006.01)

(52) U.S. Cl.
USPC ..... Plt./257

(58) Field of Classification Search
USPC ..... Plt./257
See application file for complete search history.

*Primary Examiner* — Susan McCormick Ewoldt
(74) *Attorney, Agent, or Firm* — Penny J. Aguirre

(57) ABSTRACT

A new cultivar of *Hibiscus* plant named 'TAHI16' that is characterized by its upright and well-branched plant habit, its flowers that are deep red-pink with a red eye, its large flowers that grow up to 25 cm in diameter, and its foliage that is dark green and suffused with black-purple.

2 Drawing Sheets

Botanical classification: *Hibiscus×moscheutos*.
Cultivar designation: 'TAHI16'.

CROSS REFERENCE TO RELATED APPLICATIONS

This application is co-pending with U.S. Plant Patent Applications filed for 2 plants derived from the same breeding program that are entitled *Hibiscus* Plant Named 'TAHI12' (U.S. Plant patent application Ser. No. 14/757,369) and *Hibiscus* Plant Named 'TAHI56' (U.S. Plant patent application Ser. No. 14/757,358).

BACKGROUND OF THE INVENTION

The present invention relates to a new and distinct cultivar of *Hibiscus* plant botanically known as *Hibiscus×moscheutos* 'TAHI16' and will be referred to hereafter by its cultivar name, 'TAHI16'. 'TAHI16' is a new cultivar of hardy *hibiscus* grown for use as a container and landscape plant.

The new cultivar was developed through an on-going breeding program conducted by the Inventor in Montauban, France. The new cultivar arose from a cross made in September of 2010 between *Hibiscus* 'Summer Storm' (U.S. Plant Pat. No. 20,443) as the female parent and *Hibiscus×moscheutos* 'Griotte' (not patented) as the male parent. 'TAHI16' was selected as a single unique plant in September of 2012 from the resulting seedlings of the above cross.

Asexual propagation of the new cultivar was first accomplished by softwood stem cuttings in Montauban, France in 2012 by the Inventor. Asexual propagation by softwood stem cuttings and tissue culture has determined that the characteristics of the new cultivar are stable and are reproduced true to type in successive generations.

SUMMARY OF THE INVENTION

The following traits have been repeatedly observed and represent the characteristics of 'TAHI16'. These attributes in combination distinguish 'TAHI16' as a new and distinct cultivar of *Hibiscus*.

1. 'TAHI16' exhibits an upright and well-branched plant habit.
2. 'TAHI16' exhibits flowers that are deep red-pink with a red eye.
3. 'TAHI16' exhibits large flowers that grow up to 25 cm in diameter.
4. 'TAHI16' exhibits foliage that is dark green and suffused with black-purple.

The female parent plant, 'Summer Storm', is similar to 'TAHI16' in having foliage that is dark in color and flowers that are pink in color. 'Summer Storm' differs from 'TAHI16' in having flowers that are smaller in diameter. The male parent plant, 'Griotte', is similar to 'TAHI16' in having flowers that are large in size and foliage that is dark in color. 'Griotte' differs from 'TAHI16' in having flowers that are deeper red in color, a taller plant height and foliage that is less dark in color. 'TAHI16' can be compared to cultivars that derived from the same breeding program; 'TAHI12' and 'TAHI56'. 'TAHI12' differs from 'TAHI16' in having pink flowers with more visible veins. 'TAHI56' differs from 'TAHI16' in having flowers that are very pale purple-white in color.

BRIEF DESCRIPTION OF THE DRAWINGS

The accompanying colored photographs illustrates the overall appearance and distinct characteristics of the new *Hibiscus*. The photographs were taken of a twelve month-old plant of 'TAHI16' as grown in a 23-cm container in an un-heated greenhouse in Boskoop, The Netherlands.

The photograph in FIG. 1 provides a side view of 'TAHI16' in bloom.

Figure 1:
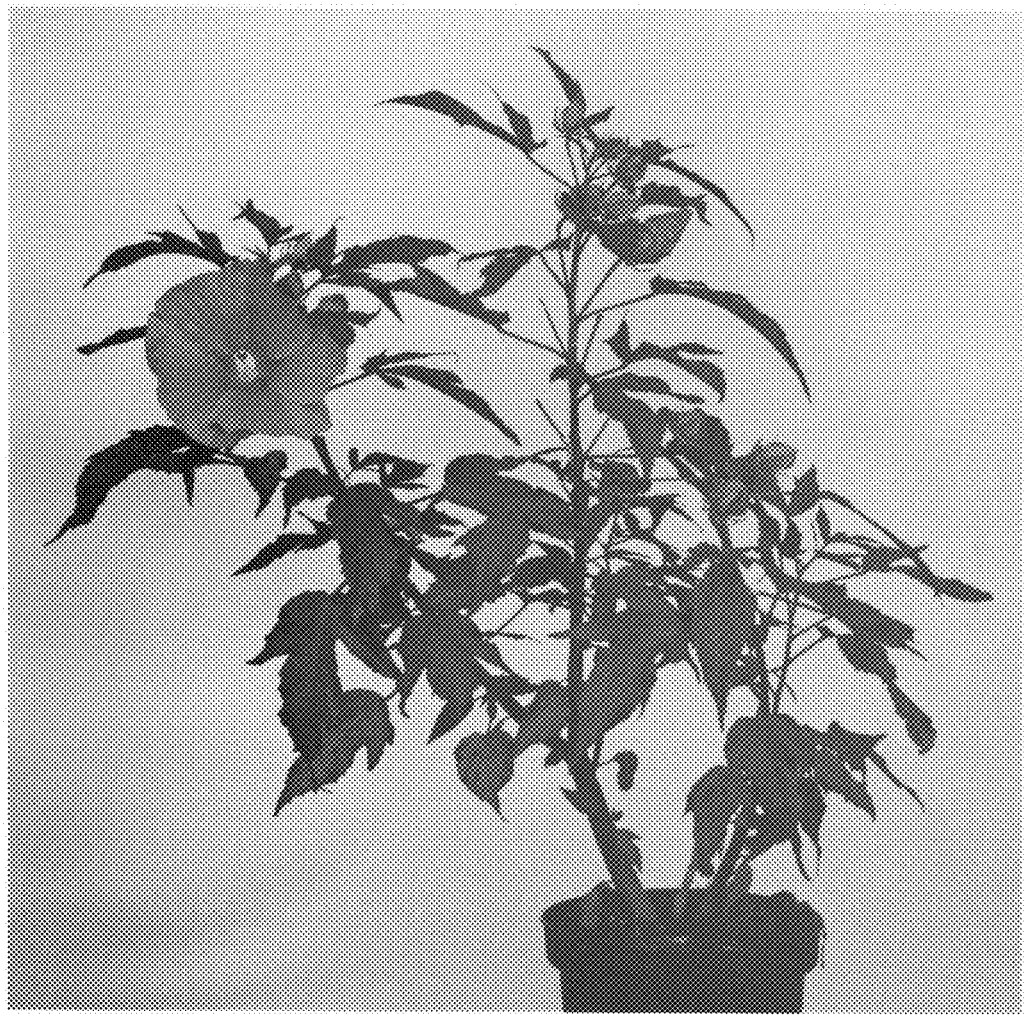
Figure 2:
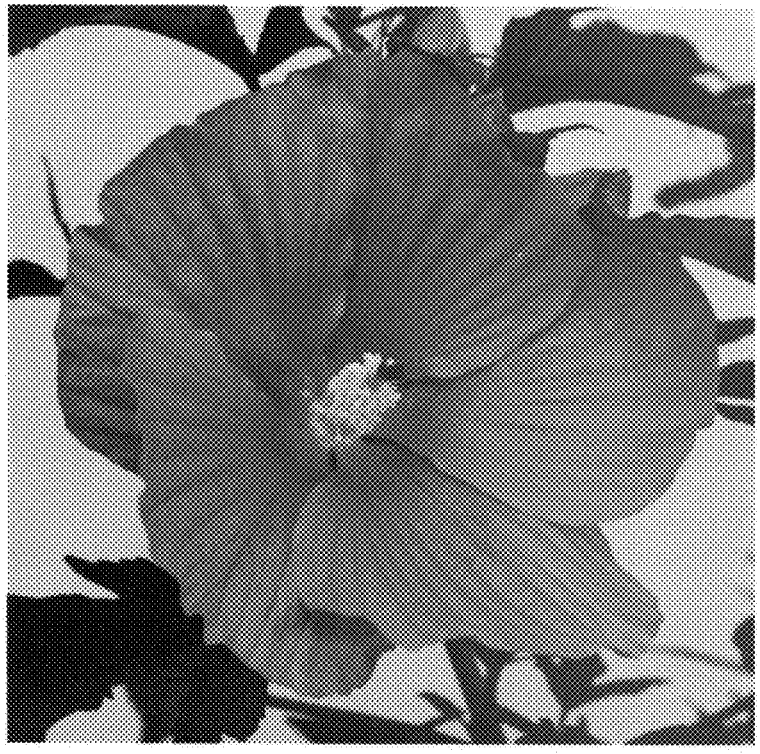

The photograph in FIG. 2 provides a close-up view of a flower of 'TAHI16'.

Figure 3:
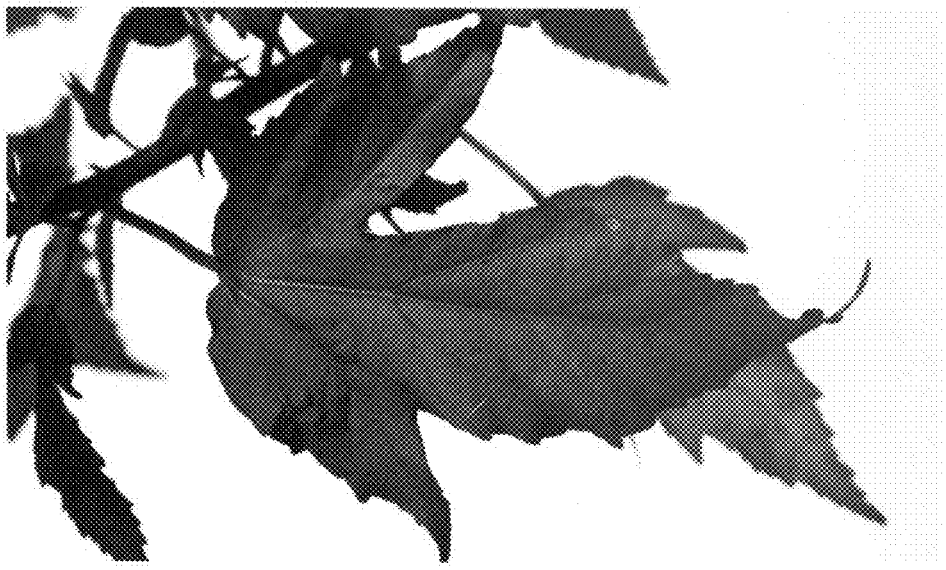

The photograph in FIG. 3 provides a close-up view of a leaf of 'TAHI16'.

The colors in the photographs are as close as possible with the digital photography and printing techniques utilized and the color codes in the detailed botanical description accurately describe the new *Hibiscus*.

DETAILED BOTANICAL DESCRIPTION OF THE PLANT

The following is a detailed description of 12 month-old plants of the new cultivar as grown outdoors in 23-cm container in Boskoop, The Netherlands. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General characteristics:

*Blooming period.*—Late summer to beginning of Autumn in The Netherlands.

*Plant type.*—Herbaceous perennial.

*Plant habit.*—Upright, well-branched.

*Height and spread.*—Reaches about 69.5 cm in height and 65 cm in spread.

*Cold hardiness.*—At least in U.S.D.A. Zone 5.

*Diseases and pests.*—No susceptibility or resistance to diseases or pests has been observed.

*Root description.*—Fibrous.

*Root development.*—Roots initiate in about 2 weeks and fully develop in about 3 months in a 4-liter container.

*Propagation.*—Softwood stem cuttings and tissue culture.

*Growth rate.*—Moderately vigorous.

Stem description:

*Shape.*—Round.

*Stem color.*—178A.

*Stem size.*—An average of 33.6 cm in length and 7 mm in diameter.

*Stem surface.*—Glabrous.

*Stem aspect.*—Upright, in an average angle of 70° (0°=vertical).

*Stem strength.*—Moderately strong.

*Branching.*—Moderately free branching, an average of 5 lateral branches.

*Internode.*—Average of 2.5 cm.

Foliage description:

*Leaf shape.*—Hastate to ovate.

*Leaf division.*—Simple.

*Leaf base.*—Hastate to truncate.

*Leaf apex.*—Long acuminate.

*Leaf venation.*—Pinnate, upper surface; 178A in color, lower surface; 181A.

*Leaf margins.*—Irregular crenate-serrate, undulate.

*Leaf attachment.*—Petiolate.

*Leaf arrangement.*—Alternate.

*Leaf orientation.*—Held upright to slightly pendulant.

*Leaf surface.*—Both surfaces glabrous, upper surface; very satiny, lower surface; matte.

*Leaf color.*—Young leaves upper surface; 143A, young leaves lower surface; 143C to 144A, mature leaves upper surface; 147A and suffused with 200A, mature leaves lower surface; 147B and slightly tinged with N186C.

*Leaf size.*—Average of 14.5 cm in length, and 11.4 cm in width.

*Leaf quantity.*—About 14 leaves per lateral branch.

*Petioles.*—Average of 5.9 cm in length, 3.5 mm in width and 3 mm in height, upper surface; 183A, lower surface; 175A, surface glabrous.

Flower description:

*Inflorescence type.*—Flowers are solitary in leaf axils.

*Lastingness of flowers.*—Average of 4 days, self cleaning.

*Flower size.*—An average of 13.6 cm in depth and 6.4 cm in diameter, up to 25 cm in spread when grown in a larger container or in the landscape.

*Flower fragrance.*—None.

*Flower shape.*—Rotate, slightly reflexed.

*Flower number.*—Average of 1 per lateral stem.

*Flower aspect.*—Outward to slightly upright.

*Flower bud.*—Ovate in shape, an average of 4 cm in length and 2.8 cm in width, color; 144A, top is 187B, glabrous surface.

*Flower attachment.*—Petiolate.

*Petal number.*—5.

*Petal shape.*—Reniform to orbicular.

*Petal color.*—Upper surface when opening; 63A, veined 53A, base N45A, lower surface when opening; between 53D and 63A, base and veins N45B, upper surface when fully open; 63A, veined 53A, base N45A, lower surface when fully open; 63B, veined 53A, base N45A.

*Petal surface.*—Both surfaces glabrous, upper side glossy, lower side matte.

*Petal margins.*—Entire.

*Petal apex.*—Obtuse.

*Petal size.*—Average of 9.2 cm in length and 9.7 cm in width.

*Sepal number.*—5.

*Sepal shape.*—Ovate.

*Sepal margin.*—Entire, overlapping.

*Sepal size.*—Average of 4 cm in length and 2.3 cm in width (measured at the base of the free part).

*Sepal aspect.*—Rotate, lower 37.5% fused.

*Sepal surface.*—Both surfaces glabrous and matte.

*Sepal apex.*—Acute.

*Sepal base.*—Broadly cuneate and fused.

*Sepal color.*—Young upper surface; 145A to 145B, young lower surface; 144A, mature upper surface; 145A to 145B, mature lower surface; 144B, tinged 183B at the top.

*Calyx.*—Rotate in shape, average of 3.6 cm in length and 6.2 cm in diameter.

*Pedicels.*—None.

*Peduncles.*—Average of 7 cm in length, 3 mm in diameter, glabrous surface, held at an average angle of 35° (0°=straight on top of lateral branch), moderately strong, color; upper side 175A, lower side tinged 146D, distal end 143C.

*Epicalyx.*—Comprised of an average of 11 bracteoles, linear in shape, curled upright, average of 2.6 cm in length and 2 mm in width, upper surface color 144C, lower surface color 144B, both sides have 174A on the tips, both surfaces are glabrous.

Reproductive organs:

*Gynoecium.*—1 pistil, average of 5.9 cm in length, stigmas; club-shaped, an average of 5 and 46A in color, style; 5.7 cm in length and 53B to 53C in color, ovary; a blend of 145D to 150D in color and completely covered by the base of the style.

*Androecium.*—Stamens; average of 120, clustered and implanted in style, anthers; dorsifixed and orbicular in shape, 1 mm in length and 196B in color; filaments; 3.5 mm in length and 155A in color, pollen; moderate to high in quantity and 8B in color.

*Fruit/seeds.*—None observed to date.

It is claimed:

1. A new and distinct cultivar of *Hibiscus* plant named 'TAHI16' as herein illustrated and described.

* * * * *